United States Patent [19]

Ritter et al.

[11] Patent Number: 4,630,617
[45] Date of Patent: Dec. 23, 1986

[54] HEART PACER LEAD WIRE WITH PULL-AWAY NEEDLE

[75] Inventors: Thomas A. Ritter, Bristol; James C. Bray, Danbury; Alan L. Kaganov, Stamford, all of Conn.

[73] Assignee: American Cyanamid Company, Stamford, Conn.

[21] Appl. No.: 195,531

[22] Filed: Oct. 9, 1980

[51] Int. Cl.[4] ............................................. A61N 1/04
[52] U.S. Cl. .................................. 128/784; 128/419 P
[58] Field of Search ........................... 128/419 P, 784

[56] References Cited

U.S. PATENT DOCUMENTS

| | | | |
|---|---|---|---|
| 1,613,206 | 1/1927 | Souttar . | |
| 2,240,330 | 4/1941 | Flagg et al. | 128/339 |
| 3,035,583 | 5/1962 | Hirsch et al. | 128/335.5 |
| 3,125,095 | 3/1964 | Kaufman et al. | 128/419 P |
| 3,474,791 | 10/1969 | Bentov | 128/419 P |
| 3,590,822 | 7/1971 | Ackerman | 128/419 P |
| 3,890,975 | 6/1975 | McGregor | 128/339 |
| 4,010,756 | 3/1977 | Dumont et al. | 128/419 P |
| 4,054,144 | 10/1977 | Hoffman et al. | 128/339 |
| 4,072,154 | 2/1978 | Anderson et al. | 128/419 P |

Primary Examiner—William E. Kamm
Attorney, Agent, or Firm—J. W. Richards; A. R. Noë; C. F. Costello, Jr.

[57] ABSTRACT

A surgical electrode consisting of an insulated stainless steel wire having surgical needles conductively affixed at one or both ends, at least one needle having a pointed end and a nonpointed end with a blind hole or flange in the nonpointed end thereof, and the blunt end of a blunt pointed pin fitted into said hole or flange and a crimp in said nonpointed end of the needle retaining said pin in said hole or flange with controlled pull-out characteristics, said pin conductively and permanently affixed at the other end to said wire, whereby said pin may be pulled out of said blind hole or flange and the blunt end of said pin used as an electrical jack for connection to a pacemaker or similar electric current generating or monitoring device. The electrodes are particularly useful as temporary heart pacer electrodes for cardiac stimulation during and after surgical operations.

8 Claims, 5 Drawing Figures

HEART PACER LEAD WIRE WITH PULL-AWAY NEEDLE

BACKGROUND OF THE INVENTION

This invention relates to surgical electrodes, and more particularly to an improvement in needled surgical electrodes to facilitate the attachment of the electrode to electrical generating or monitoring devices.

Surgical electrodes for use as heart pacer electrodes are well known in the medical profession. In general, such electrodes are constructed of a number of fine stainless steel wires twisted together to form a single flexible, multifilament electrode wire. The major portion of the wire is insulated with a polyethylene, silicone, nylon, or other non-conducting coating, with a short length of wire at either end left uninsulated. To one uninsulated end of the electrode wire there is attached by swaging or other means a fine curved needle for piercing the heart tissue to place the uninsulated end of the electrode in the myocardium. At the other end of the electrode wire is affixed a straight or Keith-type cutting needle for piercing the thoracic wall to lead the electrode to an outer point for connection with the pacemaker. Once the electrode has been properly positioned, the needles are clipped off or snapped off, as in the case of U.S. Pat. No. 4,010,756, and the uninsulated end of the electrode is ready for attachment to the pacemaker as required for stimulating or regulating the beating of the heart.

Insulated stainless steel sutures and their application as heart pacer electrode wires are described generally in U.S. Pat. Nos. 3,035,583; 3,125,095 and 3,847,156, which patents are incorporated herein by reference.

The electrodes of the prior art have disadvantages in that when the electrode has been positioned for heart stimulation, the needle on the end exterior to the body must be clipped off and the bare stainless steel wire then attached in electrical contact to the pacemaker unit, or the needle itself must be snapped off and the remaining attached shank used as an electrical jack for connection to the pacemaker unit. The steps of needle removal and wire attachment are separate, time consuming acts at a critical stage of the heart surgery. Moreover, upon repeated attachment, removal and reattachment, the ends of the stainless steel wire may fray and become difficult to work with. In the snap-off or break-away lead wire disclosed in U.S. Pat. No. 4,010,756, there is always the danger that there may be sharp edges on the electrical jack portion of the needle which might tear the surgeon's gloves and compromise the sterile field or that the pacemaker may be damaged when the shank of the needle is inserted therein.

The present invention works an improvement over the prior art by simplifying and/or refining the attachment, removal and reattachment of the electrode to the pacemaker. It is accordingly an object of the present invention to provide a surgical electrode having a needle which can be removed without cutting or breaking. It is a further object of this invention to provide a surgical electrode which is quickly and easily attached to a pacemaker after removal of the needle. It is yet a further object of this invention to provide surgical electrodes having blunt pointed electrical connecting means adapted for pacemaker electrical devices.

SUMMARY

A conventional surgical electrode wire is equipped with a specially designed, blunt pointed electrical connector pin, the blunt point of which is inserted into the drilled or flanged end of a straight cutting needle and attached thereto by a crimping procedure allowing for controlled pull-out characteristics for the connector pin. The other end of the connector pin is attached to and in electrical contact with the conductive electrode wire. Following placement of the electrode in the patient, the connector pin is pulled away from the needle whereon the needle is discarded and the blunt portion of the connector pin conveniently connected to an electrical stimulation or monitoring device.

The present invention provides for an electrical connector needle assembly to be utilized in temporary cardiac pacer wires. It provides a unit or assembly which contains a disposable needle and an electrical connector pin serving as a electrical jack which can be conveniently and easily separated when necessary.

In the practice of the present invention, one end of an insulated wire, such as a multifilament stainless steel wire coated with a dielectric insulating plastic, is stripped a short length to expose the steel wire. The exposed wire is permanently attached to one end of a blunt pointed connector pin capable of carrying electrical current and the blunt end of the pin inserted into the drilled or flanged end of a straight cutting needle. The attachment can be in either a "drilled end" needle, that is one in which a concentric hole is formed in the end of the needle in which the pin is placed and the needle crimped around the pin; or in a "flange" needle in which a U-shaped channel is stamped into the end of the needle with the ends of the U being crimped about the pin to hold the pin. The pin and needle attachment is achieved with crimping procedures to the desired pull-off force, such as that disclosed in U.S. Pat. No. 4,054,144, incorporated herein by reference thereto. To discard the cutting needle, the pin and needle are pulled apart, the needle discarded, and the blunt end of the pin remains for connection to an external pulse generator.

DESCRIPTION OF THE PREFERRED EMBODIMENTS

The surgical electrodes of the present invention have at least one eyeless needle conductively attached to the electrode wire. Specifically, the novel heart pacer lead wire of the present invention is characterized by having an electrical connector pin with a blunt end, the blunt end of which is adapted to fit into a coaxial cylindrical blind hole in the drilled or flanged end of a surgical needle which can be crimped to give controlled pull-out characteristics yet retain the pin in the hole or flange until pulled out, and a lead wire receiving end, with a drilled or flanged coaxial cylindrical blind hole in said end, for attachment of an electrode wire by crimping.

Figure 1:
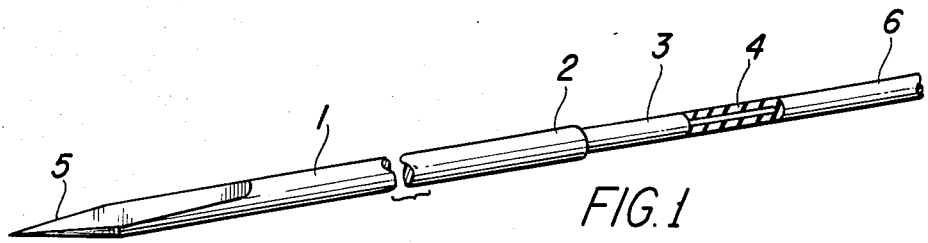
FIG. 1 is the end of the electrode intended for attachment to the pacemaker showing the assembled unit with the electrical connector pin crimped in the needle.

With specific reference to FIG. 1 of the drawing, needle 1 has a straight shank end 2 attached to and in electrical contact with blunt point connector pin 3 by removably crimping shank end 2 to pin 3 and the other end of pin 3 is in turn attached to and in electrical contact with wire 4 by permanently crimping wire 4 to pin 3. Pointed end 5 of needle 1 has a cutting edge designed for piercing the thoracic wall of the patient.

Figure 3:
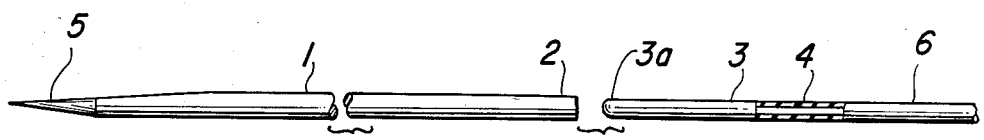
FIG. 3 shows the pin after it has been pulled away from the needle.

When the electrode has been positioned in the patient and is ready for attachment to the pacemaker device, needle 1 is grasped and pulled apart at shank end 2 as shown in FIG. 3. Alternatively, needle 1 and pin 3 may be grasped and, by application of a bending movement, the blunt pointed teat of pin 3 may be broken off the end of pin 3. The teat remains in shank end 2. Needle 1 is discarded while pin 3 with attached electrode is readily inserted into a properly sized receptacle in the pacemaker device by inserting blunt end 3(a) therein. Pin 3 represents a unified structure which may be quickly and readily attached, removed and reattached to the pacemaker as required without encountering frayed ends characteristic of a bare, multifilament stainless steel wire or the sharp ends of a snapped needle.

Needle 1 is conventionally straight and of a circular cross-section. For purposes of the instant invention, however, the configuration of pointed end 5 is immaterial and it may be curved, straight, or in any desired configuration.

Connector pin 3 is preferably straight for convenient insertion into the connecting receptacle on the pacemaker, but may be of any desired cross-sectional configuration. While a circular cross-section is generally preferred, pin 3 may be triangular, rectangular, or square and such cross-sections may be particularly useful where the electrode is intended to be connected to a particular electrical device, and the needle is desirably designed to fit that particular device and no other.

Figure 5:
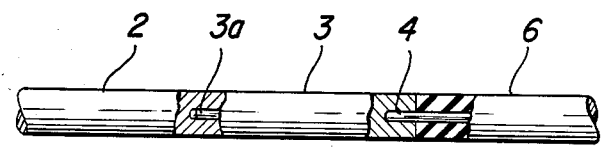
FIG. 5 shows a preferred embodiment of the surgical electrode wherein the electrical connector pin terminates in a blunt pointed teat and the insulated wire and needle are all the same diameter.

In the preferred embodiment shown in FIG. 5, insulation 6 and connector pin 3 are approximately the same diameter as shank end 2 and pin 3 terminates in a blunt pointed teat. The teat serves to anchor pin 3 to shank end 2 when crimped. This has the added advantage of providing a smooth and continuous surface to facilitate threading the electrode through the thoracic wall. Pin 3 can be stainless steel or other conductive material and of any desired length. Pin 3 may contain a drilled end or a flanged end to receive wire 4, preferably a drilled end.

Figure 4:
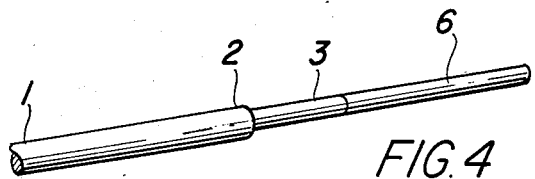
FIG. 4 shows an embodiment of the surgical electrode wherein the insulation is continuous from the pin to the suture wire.

Since pin 3 is used for making electrical connection with the electrical device, insulation 6 of wire 4 may extend up to or even over the end of pin 3, or be inserted into the hole in pin 3. Abutting the insulation to pin 3 as shown in FIG. 4 also has the added advantage of providing a relatively smooth, continuous and sealed exterior surface to facilitate threading the electrode through the thoracic wall and to exclude contamination from the interior of the electrode. In the sutures of the prior art, it has been necessary to provide a segment of uninsulated suture adjacent the needle to allow for electrical connection to the pacemaker after the needle has been clipped off the wire, or to take an extra step of stripping insulation from the wire to provide an electrical connection.

Electrically conductive wire 4 can be any flexible electrically conductive wire. The preferred electrically conductive wire is mono- or multifilament stainless steel wire, preferably multifilament or twisted stainless steel wire.

Insulation 6 may be any dielectric insulating plastic coating such as fluoronated ethylene propylene (FEP) copolymer TEFLON® variant (TEFLON® type 100), polyethylene or nylon.

Figure 2:
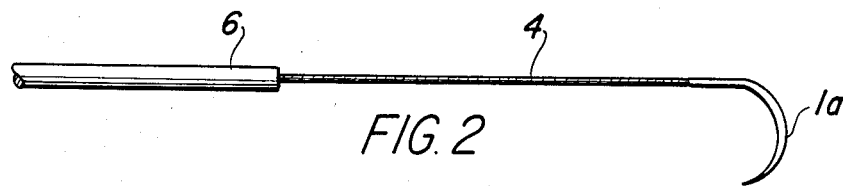
FIG. 2 is the end of the electrode intended for attachment to the heart and having a fine, curved needle for piercing the myocardium.

The end of the electrode intended for connection to the heart has a fine, curved or other needle attached to a length of uninsulated wire as shown in FIG. 2. The needle is passed through the ventricular myocardium and the wire is drawn through until the insulated portion of the electrode abuts the surface of the heart. The electrode is anchored to the heart and the needle and excess suture wire are then clipped off leaving a length of uninsulated wire within the myocardium and in electrical contact therewith.

The special, pull-away needles of the present invention may be specifically illustrated by the following:

A strand of Teflon® coated Flexon® 0.0018 inch braided stainless steel suture wire is stripped of the Teflon® insulation to expose about 1/16 inch of wire. This stripped end of wire is then inserted into a coaxial cylindrical blind hole having a diameter of about 0182/0.0192 inch in one end of a stainless steel blunt pointed pin having a length of about ⅜ inch and a diameter of about 0.028 inch. This pin is then secured or attached to the wire with about 5 pounds holding strength and the other blunt end of the pin inserted into a coaxial cylindrical blind hole having a diameter of about 0.039 inch. The needle is then crimped over the pin with a holding strength of about 0.028 kilograms to about 1.59 kilograms.

Several variants have been developed over that specifically illustrated above which allow for the use of a smaller, straight needle. A 0.034 straight cutting needle has been removably crimped, as above, to the connector pin as shown in FIG. 5.

We claim:

1. A surgical electrode comprising:
   (a) an electrically conductive wire having a first needle attached to and in electrical contact with one end of said wire;
   (b) an electrically conductive connector pin permanently attached to and in electrical contact with the other end of said wire and having a blunt pointed end opposite the end attached to said wire;
   (c) a second needle having a cylindrical blind hole in one end into which is inserted, with removable attachment and in electrical contact, the blunt pointed end of said pin; and
   (d) a dielectric insulating coating over the exterior surface of said wire electrically insulating said wire over a major portion of the length thereof;
   the removable attachment being such that the needle and pin may be readily pulled away from each other.

2. An electrode of claim 1 wherein the dielectric insulating coating over the exterior surface of the wire is continuous from the surface of said pin.

3. An electrode of claim 1 wherein said conductive wire is a multifilament stainless steel strand.

4. An electrode of claim 1 wherein said pin is attached to the second needle with crimping providing a controlled pull-out of predetermined force.

5. An electrode of claim 1 wherein said first needle is a curved needle.

6. An electrode of claim 1 wherein said second needle is a straight cutting needle.

7. A surgical electrode comprising:
(a) an electrically conductive wire having a first needle attached to and in electrical contact with one end of said wire;
(b) an electrically conductive connector pin containing a portion of the other end of said wire permanently crimped into a coaxial cylindrical blind hole in one end of said pin and having a blunt point on the other end of said pin;
(c) a second needle containing the blunt end of said pin removably crimped into a coaxial cylindrical blind hole in the nonpointed end of said needle such that said needle and pin may be readily pulled away from each other; and
(d) a dielectric insulating coating over the exterior surface of said wire electrically insulating said wire continuous from the surface of said pin.

8. A surgical electrode comprising:
(a) a multifilament stainless steel wire having a curved needle attached to and in electrical contact with one end of said wire;
(b) a stainless steel connector pin containing a portion of the other end of said wire permanently crimped into a coaxial cylindrical blind hole in one end of said pin and having a blunt point on the other end of said pin terminating in a blunt pointed teat;
(c) a straight cutting needle containing the blunt pointed teat of said pin removably crimped into a coaxial cylindrical blind hole in the nonpointed end of said needle, such that said needle and pin may be readily pulled away from each other, said pin and needle being of substantially the same diameter; and
(d) a TEFLON ® type 100 coating over the exterior surface of said wire continuous from the surface of said pin.

* * * * *